United States Patent [19]

November

[11] 4,064,738
[45] Dec. 27, 1977

[54] VIBRATION DENSITOMETER

[75] Inventor: Milton H. November, Hacienda Heights, Calif.

[73] Assignee: International Telephone and Telegraph Corporation, New York, N.Y.

[21] Appl. No.: 766,265

[22] Filed: Feb. 7, 1977

[51] Int. Cl.² ............................................. G01N 9/00
[52] U.S. Cl. .................................................. 73/32 A
[58] Field of Search ................................. 73/30, 32 A

[56] References Cited

U.S. PATENT DOCUMENTS

| 3,218,851 | 11/1965 | Sipin | 73/32 A X |
| 3,808,875 | 5/1974 | Miller | 73/32 A |

Primary Examiner—James J. Gill
Attorney, Agent, or Firm—A. Donald Stolzy

[57] ABSTRACT

A vibration densitometer having a probe including a hollow cylinder.

2 Claims, 8 Drawing Figures

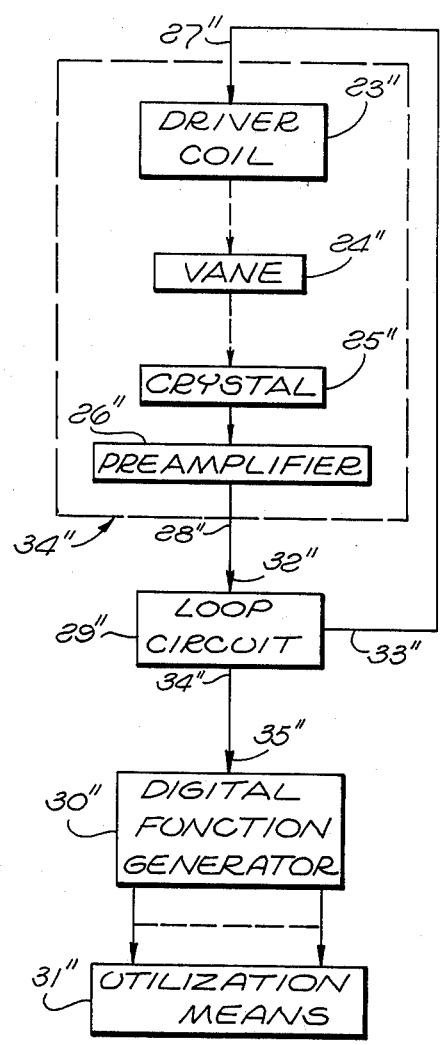
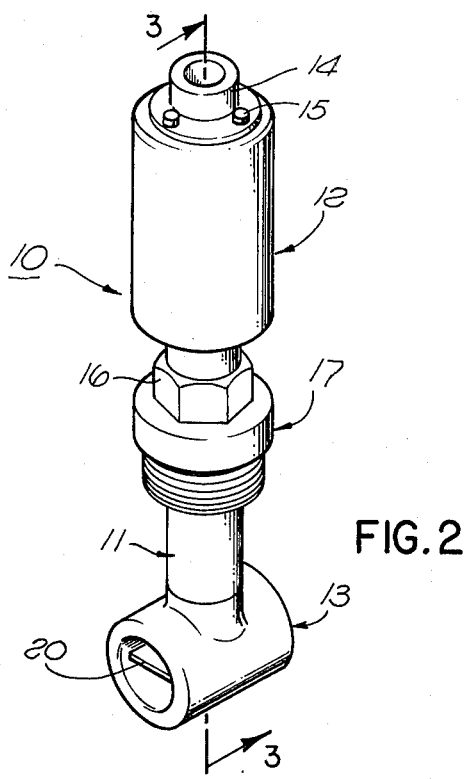
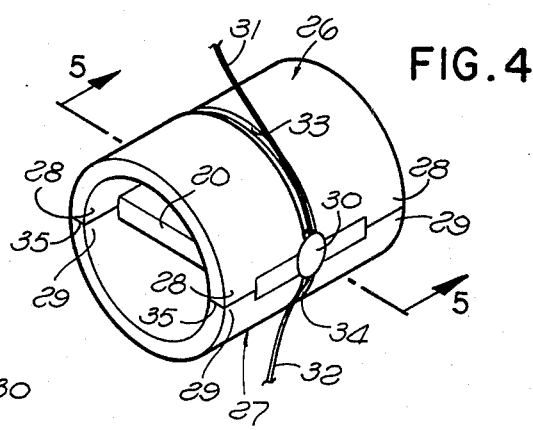
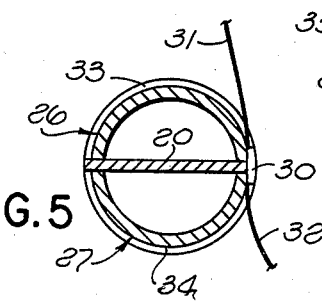
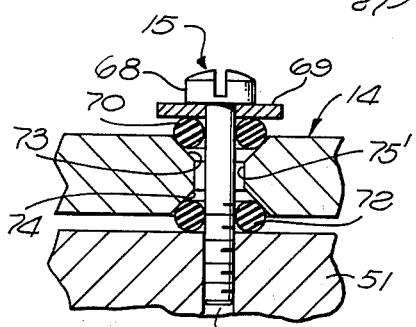
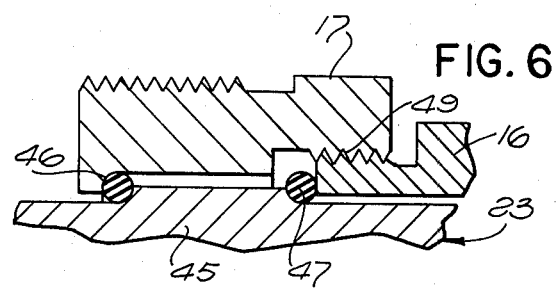

VIBRATION DENSITOMETER

BACKGROUND OF THE INVENTION

This invention relates to devices for producing an output which is a function of fluid density, and more particularly, to a vibration densitometer and a probe therefor.

SUMMARY OF THE INVENTION

In accordance with the device of the present invention, disadvantages of the prior art are overcome by providing a vibration densitometer comprising: an electromechanical oscillator including a probe and a feedback circuit connected in a loop; a function generator connected from said feedback circuit; and utilization means connected from said function generator, said probe including inner and outer concentric cylinders fixed relative to each other, said outer cylinder having a hole extending radially therethrough, a shaft slidable through said hole in engagement with said inner cylinder and means to vibrate said shaft in the direction of its axis to cause vibration of said inner cylinder, both cylinders being hollow completely therethrough.

The above-described and other advantages of the present invention will be better understood from the folowing detailed description when considered in connection with the accompanying drawings.

BRIEF DESCRIPTION OF THE DRAWINGS

In the drawings which are to be regarded as merely illustrative:

FIG. 1 is a block diagram of a densitometer constructed in accordance with the present invention;

FIG. 2 is a perspective view of a densitometer probe;

FIG. 4 is a perspective view of a group of conponent parts of the probe shown in FIG. 2;

FIG. 5 is a transverse sectional view of the assembly taken on the line 5—5 shown in FIG. 4;

FIG. 6 is an enlarged longitudinal sectional view of a portion of the probe shown in FIG. 2;

FIG. 7 is a longitudinal sectional view of a portion of mounting means for an electrical connector otherwise substantially fixed relative to the probe taken on the line 7—7 shown in FIG. 3.

DESCRITPTION OF THE PREFERRED EMBODIMENT

Figure 3:
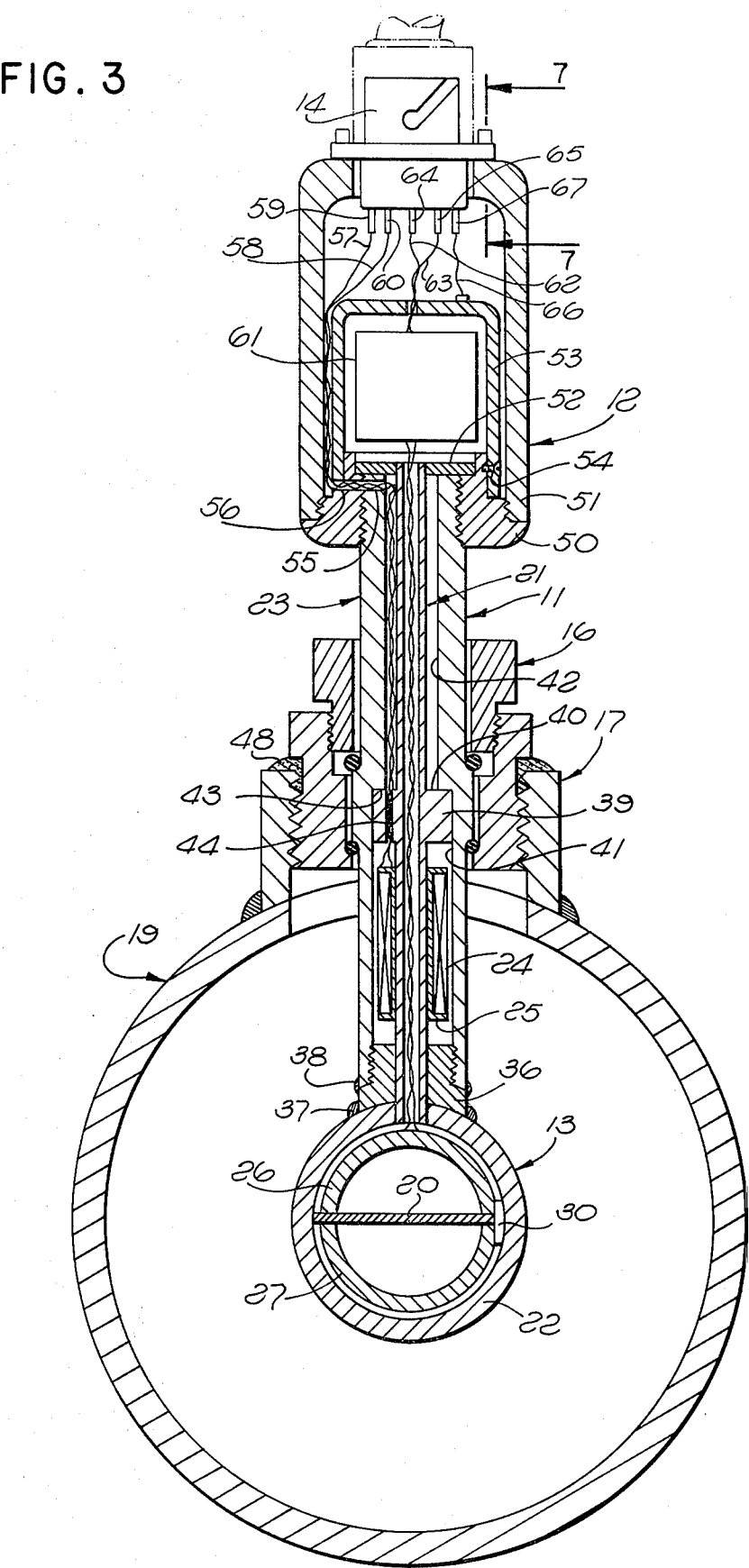
FIG. 3 is a sectional view of the probe taken on the line 3—3 shown in FIG. 2.

In the drawings, in FIG. 1, a vibration densitometer probe is indicated at 34''' having a driver coil 23'', a vane 24'', a piezoelectric crystal 25'' and a preamplifier 26''.

Probe 34''' has an input lead 27'' and an output lead 28''.

Other blocks shown in FIG. 1 are a loop circuit 29'', a digital function generator 30'' and utilization means 31''. Loop circuit 29'' has an input lead 32'' and output leads 33'' and 34''. Digital function generator 30'' has an input lead 35'' connected from loop circuit output lead 34''. The output of digital function generator 30'' is connected to utilization means 31''.

The output lead 28'' of probe 34''' is connected to the input lead 32'' of loop circuit 29''. The input lead 27'' of probe 34''' is connected from the output lead 33'' of loop circuit 29''. Probe 34''' and loop circuit 29'' form a closed loop electromechanical oscillator. Vane 24'' is submerged in a fluid. The density of the fluid is a function of the frequency at which vane 24'' vibrates.

Digital function generator 30'' may have its input lead 35'' connected from lead 33'' or at other points in loop circuit 29''. Loop circuit 29'' impresses a square wave voltage on input lead 35'' of digital function generator 30'' having a mark-to-space ratio of 1:1.

Utilization means 31'' shown in FIG. 1 may be a density indicator, a specific gravity indicator, a process controller or otherwise.

Throughout this description, reference will be made to the text of certain U.S. patents and U.S. patent applications. These patents and patent applications are listed for convenience forthwith.

The following patents are hereby incorporated by reference herein:
1. U.S. Pat. No. 3,677,067.
2. U.S. Pat. No. 3,706,220.
3. U.S. Pat. No. 3,738,155. 4. U.S. Pat. No. 3,741,000.
5. U.S. Pat. No. 3,878,374.

The foregoing patents of paragraphs (1), (2), (3) and (4) are hereinafter referred to as patents P1, P2, P3, P4 and P5, respectively.

Figure 8:
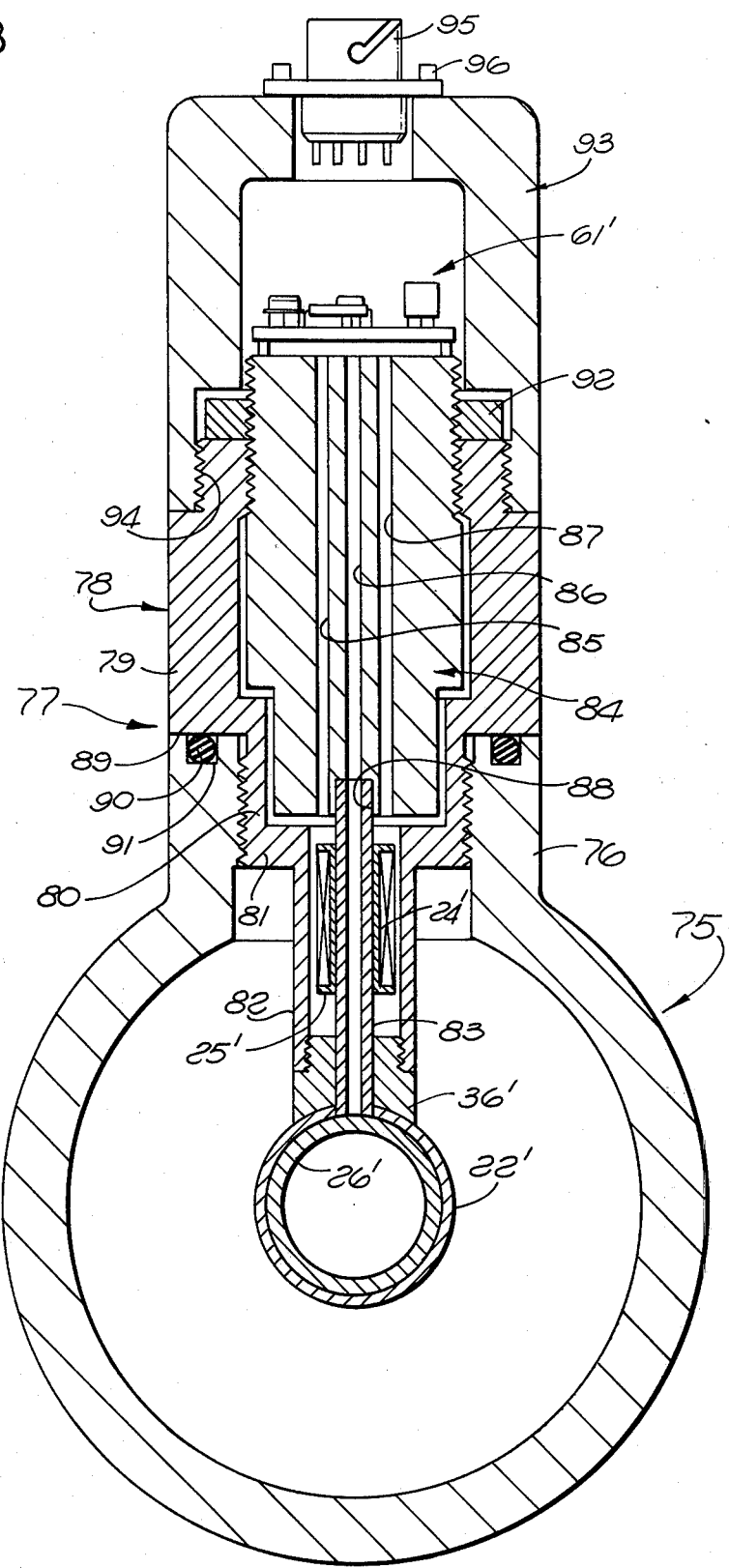
FIG. 8 is a longitudinal sectional view through a densitometer probe constructed in accordance with the present invention.

Probe 34''' shown in FIG. 1 is conventional. The probe of the present invention is shown in FIG. 8.

FIGS. 1-7, inclusive, are prior art.

In FIG. 2, a probe is indicated at 10 havng a shank 11, a housing 12 at its upper end, a tubular assembly 13 at its lower end, and an electrical connector assembly 14 at the upper end of housing 12 fixed thereto by bolts 15. Annular fittings 16 and 17 extend around shank 11 for mounting probe 10 in a hollow cylindrical extension 18 of a pipeline 19, as shown in FIG. 3.

As shown in FIGS. 2 and 3, a stainless steel vane 20 is mounted in assembly 13 in a position perpendicular to the axis of a hollow cylindrical magnetostrictive inner tube 21. Vane 20, if desired, may be also mounted in a symmetrical position with respect to the axis of an outer sleeve 22 which houses it.

Vane 20 may be a rectangular plate having flat and parallel upper and lower surfaces as shown in FIG. 3, and may otherwise have mutually normal surfaces forming a right parallelopiped.

Shank 11 not only includes inner tube 21, but an outer magnetic tube 23. A driver coil or solenoid winding 24 wound on a nylon bobbin 25 is press fit onto the external surface of inner tube 21 and located in a space between the tubes 21 and 23 toward the lower end of shank 11. Coil 24 is thus maintained in a substantially fixed position on inner tube 21, although the same is not necessarily critical to the operation of the device of the present invention.

Vane 20 is supported between two half cylinders 26 and 27 as shown in FIGS. 3 and 4. According to the invention, the longitudinal edges of vane 20 are pressed together between half cylinders 26 and 27 with a pressure of, for example, 20,000 pounds per square inch because the assembly shown in FIG. 4 is inserted in sleeve 22 with an interference fit, sleeve 22 being heated prior to the said insertion.

Half cylinder 26 has four projections 28, and half cylinder 27 has four projections 29. Projections 28 and 29 serve to prevent longitudinal movement of vane 20 between half cylinder 26 and half cylinder 27 although the same is not likely due to the clamping pressure on vane 20 between half cylinder 26 and half cylinder 27.

Half cylinders 26 and 27 and vane 20 may be machined to have a flat or recess or receive a piezoelectric crystal 30. Crystal 30 has electrical leads 31 and 32 which extend around half cylinders 26 and 27 in grooves 33 and 34, respectively, to a point where they enter the hollow interior of inner tube 21. This entry is made at the lower end of inner tube 21, as shown in FIG. 3.

As shown in FIG. 4, projections 28 and 29 may have a slight separation at 35 to insure that the pressure contact of half cylinders 26 and 27 on vane 20 is quite high due to the said interference fit.

As shown in FIG. 3, a boss 36 is welded at 37 to sleeve 22 in a fluid tight manner. Although the device of the present invention need not always be fluid tight throughout, a glass-to-metal seal or other seal may be provided inside innertube 21 for leads 31 and 32. Before the said interference fit is provided, if desired, crystal 30, and those portions of leads 31 and 32 in grooves 33 and 34, respectively, may be potted with an epoxy. Further, after the interference fit has been effected, the entire unit, when completely assembled, may be treated further by applying a bonding agent around all of the structures inside sleeve 22. Any conventional bonding process may be employed including, but not limited to, the application of a bonding agent sold under the name of "Locktite."

As stated previously, boss 36 may be welded to sleeve 22 at 37 in a fluid tight manner. Further, outer tube 23 may be threaded onto boss 36 and welded thereto at 38 in a fluid tight manner. For all practical purposes, boss 36 may thus be considered an integral part of outer tube 23. Boss 36, for example, is also made of a magnetic material. All of the "magnetic materials" referred to herein may be any magnetic material including, but not limited to, any stainless steel or 416 stainless steel. However, inner tube 21, although being magnetic, must also be magnetostrictive. Notwithstanding this limitation, it is to be noted that inner tube 21 is employed to produce vibration, and if one feature of the present invention is used without another, the use of a magnetostrictive or magnetic material may not be required, and the invention still practiced.

Inner tube 21 has an annular projection 39 with a shoulder 40. Outer tube 23 has a lower bore 41 separated from a smaller upper counter bore 42 by an annular shoulder 43. Shoulders 40 and 43 abut. From shoulder 40 to the lower end of inner tube 21, inner tube 21 is always in axial compression. That is, inner tube 21 is in compression when coil 24 is energized, but inner tube 21 is also in compression when coil 24 is deenergized. Coil 24 is energized with a varying D.C. current or otherwise which thus merely changes the degree of compression of inner tube 21.

Projection 39 has a hole 44 through which the electrical leads of coil 24 can pass from the location of coil 24 upwardly between tubes 21 and 23.

The manner in which probe 10 is mounted in pipeline 19 is better illustrated in FIG. 6. In FIG. 6, note will be taken that outer tube 23 has an outwardly extending radial projection 45 on each side of which rubber O-rings 46 and 47 are compressed by fittings 16 and 17. Fitting 17 is threaded into extension 18 and sealed thereto by a conventional sealing compound 48 shown in FIG. 3. In FIG. 6, note will be taken that fitting 16 is threaded inside fitting 17 at 49. The amount O-rings 46 and 47 are compressed is, therefore, determined by the position of fitting 16. That is, fitting 16 is turned, for example, by a wrench, until the desired O-ring compression is reached.

From the construction illustrated in FIG. 6, note will be taken that only O-rings 46 and 47 contact outer tube 23, and that, therefore, shank 11 is never touched by either fitting 16 or fitting 17.

It is an advantage of the present invention that the construction of probe 10 is such that the leads from coil 24 are kept magnetically separate from the leads from crystal 30. This is true through a portion of housing 12 as will be described. Housing 12 has a fitting 50 threaded onto outer tube 23. A cylinder 51 is threaded to fitting 50. A washer 52 is press fit and thereby fixed in fitting 50 and around inner tube 21. Inner tube 21 has an upper end which may be fixed relative to or slidable in washer 52, as desired. However, preferably the external surface of inner tube 21 at its upper end fits contiguous or in contact or in pressure contact with the surface of washer 52 defining the hole therethrough. A shield 53 made of a magnetic material may be fixed around fitting 50 by one or two or more screws 54. Outer tube 23 has a radial hole 55 therethrough through which the leads from coil 24 pass. Fitting 50 has a hole 56 therethrough in alignment with hole 55 through which the leads from coil 24 pass. From the outward radial extremity of hole 56, the coil leads indicated at 57 and 58 pass upwardly between cylinders 51 and shield 53 and are connected to pins 59 and 60 of the electrical connector 14. Electrical connector 14 may be a conventional five pin connector.

As stated previously, the leads 31 and 32 from crystal 30 extend upwardly through the interior of inner tube 21. At the upper end of inner tube 21, as shown in FIG. 3, leads 31 and 32 are connected to the input of differential amplifier 61. Leads 31 and 32 thus extend outwardly through the upper opening in inner tube 21.

Differential amplifier 61 may be entirely conventional, and mounted on a conventional card, if desired. Amplifier 61 may be supported inside shield 53 by any conventional means, if desired, or simply supported by the strength of leads 31 and 32, and output leads 62 and 63 which are connected to pins 64 and 65 of connector 14, respectively. A lead 66 provides a ground connection from shield 53 to the fifth pin 67 of connector 14.

The manner in which connector 14 is mounted on cylinder 51 is shown in FIG. 7. Only one bolt 15 is shown in FIG. 7 since all bolts 15 are similarly situated. In FIG. 7, bolt 15 is shown having a head 68, a washer 69 under head 68, an O-ring 70 under washer 69 and a shank 71 threaded into cylinder 51. A second O-ring 72 also extends around screw shank 71. O-ring 70 fits between the lower surface of washer 69 and a counter sunk frusto-conical hole 73 in connector 14. O-ring 72 fits between the upper surface of cylinder 51 and another counter sunk frusto-conical hole 74 in connector 14. Holes 73 and 74 are connected by a bore 75'. Form FIG. 7, it will be noted that all the structures shown therein may vibrate, but that the amount of vibration transmitted to connector 14 may be quite small.

According to an outstanding feature of the present invention, the more complicated resilient mount of the probe 10, shown in FIG. 3, is avoided by the construction shown in FIG. 8.

In FIG. 8, a pipeline is indicated at 75 having a hollow boss 76 in which a probe 77 is located.

Probe 77 has a housing 78 including an upper heavier portion 79, an intermediate portion 80, a transverse portion 81 and a hollow portion 82. A small portion 83 extends below portion 79. All of the portions 79, 80, 81 and 82 are integral with one another.

Parts 22', 26' and 36' may, if desired, be similar to parts 22, 26 and 36, respectively, shown in FIG. 3.

Part 26' has grooves 33 and 34 therein, but these are not shown in FIG. 8 for clarity. The same is true of a crystal similar to crystal 30 and all of the electrical leads. Probe 77 has no vane.

As before, boss 36' forms a hollow cylinder or ferrule which has a reduced diameter portion at its upper end to which housing portion 82 is threaded.

Magnetostrictive tube 83 has its lower end slidable through ferrule 36' and cylinder 22'. Tube 83 lies in engagement with an upper portion of the external cylindrical surface of cylinder 26'. The lower end of tube 83 is not bonded to the cylinder 26'.

The upper end of tube 83 is press fit into a supporting body 84. Body 84 has three holes 85, 86 and 87 extending completely therethrough in a vertical or axial direction. Body 84 has a counter bore 88 into which tube 83 is press fit, as aforesaid.

The external surface of housing portion 80 is threaded into boss 76. Housing 78 may thus be fixed rigidly relative to pipeline 75. Housing portion 79 has a shoulder 89 which abuts the upper end of boss 76. An O-ring 90 is located in a groove 91 in the upper end of boss 76 to provide a fluid tight seal thereat.

As before, a spool 25' identical to spool 25 is press fit on tube 83. Spool 25' carries a coil 24' identical to coil 24.

The passages 85 and 87 are provided in body 84 for the coil leads. The passage 86 in body 84 aligns with the hole through tube 83 to provide a path through which the crystal leads may be threaded.

Although it is not critical which particular types of materials are employed for body 84, housing 78 and tube 83, preferably tube 83 is made of "Ni Span C" which normally has a density between 2.89 and 2.91 pounds per cubic inch. Preferably housing 78 and body 84 are made of a magnetic material such as 416 stainless steel which has a density of about 2.78 pounds per cubic inch.

Housing portion 79 is internally and externally threaded. The upper end of body 84 is threaded into housing portion 79. A jam nut 92 holds body 84 in a fixed position relative to housing 78.

A differential amplifier 61' is fixed relative to body 84 and may be identical to amplifier 61, shown diagrammatically in FIG. 3. An end cap 93 has an internal thread 94 which is threaded externally to housing portion 79. A conventional electrical connector 95 is fixed to cap 93 by bolts 96. A resilient mounting for connector 95 is thus not required as illustrated in FIGS. 3 and 7 for electrical connector 14.

In the assembly of the portion of FIG. 8, before end cap 93 is assembled to housing 78, and before jam nut 92 is threaded onto the upper end of body 84, body 84 is turned by hand, i.e. with the fingers, until tube 83 is placed in moderate compression against cylinder 26'. Jam nut 92 is then run down tight against the upper end of housing 78 and cap 93 is threaded thereto.

In FIG. 8, although cylinder 26' vibrates, it is not necessarily the only structure of the probe that vibrates.

What is claimed is:

1. A vibration densitometer comprising: an electromechanical oscillator including a probe and a feedback circuit connected in a loop; a function generator connected from said feedback circuit; and utilization means connected from said function generator, said probe including inner and outer concentric cylinders fixed relative to each other, said outer cylinder having a hole extending radially therethrough, a shaft slidable through said hole in engagement with said inner cylinder, and means to vibrate said shaft in the direction of its axis to cause vibration of said inner cylinder, said outer cylinder being completely hollow except for said inner cylinder positioned therein, said inner cylinder being hollow completely therethrough.

2. The invention as defined in claim 1, wherein said utilization means includes an indicator calibrated in density.

* * * * *